(12) United States Patent
Zeyss et al.

(10) Patent No.: US 7,015,355 B2
(45) Date of Patent: Mar. 21, 2006

(54) METHOD FOR THE SELECTIVE PRODUCTION OF ACETIC ACID BY CATALYTIC OXIDATION OF ETHANE AND/OR ETHYLENE

(75) Inventors: Sabine Zeyss, Königstein (DE); Uwe Dingerdissen, Seeheim-Jugenheim (DE)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 10/258,758

(22) PCT Filed: May 3, 2001

(86) PCT No.: PCT/EP01/04987

§ 371 (c)(1),
(2), (4) Date: Nov. 19, 2002

(87) PCT Pub. No.: WO01/90039

PCT Pub. Date: Nov. 29, 2001

(65) Prior Publication Data

US 2003/0158440 A1    Aug. 21, 2003

(30) Foreign Application Priority Data

May 19, 2000   (DE) ................................ 100 24 437

(51) Int. Cl.
*C07C 51/16* (2006.01)
(52) U.S. Cl. ....................... 562/548; 562/543; 562/544
(58) Field of Classification Search ................ 560/606, 560/607; 502/300, 305, 311
See application file for complete search history.

(56) References Cited

U.S. PATENT DOCUMENTS 5,049,692 A    9/1991   Hatano et al.
6,399,816 B1 *  6/2002   Borchert et al. ......... 562/512.2

FOREIGN PATENT DOCUMENTS

DE   19745902   4/1999
EP    0395809   2/1999

* cited by examiner

*Primary Examiner*—Johann Richter
*Assistant Examiner*—Karl Puttlitz
(74) *Attorney, Agent, or Firm*—Charles A. Muserlian

(57) ABSTRACT

A method for the selective production of acetic acid from a gas-phase feed of ethane, ethylene, or mixtures thereof and oxygen at elevated temperatures. The gas-phase feed is brought into contact with a catalyst, containing the elements Mo, Pd, X and Y in the gram atom ratios a:b:c: in combination with oxygen according to formula (I): $MO_aPd_bX_cY_d$. The symbols X and Y have the following meanings: X=one or several elements chosen from the group Cr, Mn, Nb, Ta, Ti, V, Te and W; Y=one or several elements chosen from the group B, Al, Ga, In, Pt, Zn, Cd, Bi, Ce, Co, Rh, Ir, Cu, Ag, Au, Fe, Fu, Os, K, Rb, Cs, Mg, Ca, Sr, Ba, Nb, Zr, Hf, Ni, P, Pb, Sb, Si, Sn, Ti and U: the indices a, b, c, d and x=the gram atom ration for the corresponding elements, where: a=1; b—0.0001 to 0.01; c=0.4 to 1; and d=0.005 to 1, wherein the space-time yield for the above oxidation to yield acetic acid is 470 kg/(hm$^3$) and the selectivity of the oxidative reaction of ethane and/or ethylene to give acetic acid is, in particular, $\geq 70$ mol %. X=preferably Nb and an ammonium salt of niobium is used as niobium source.

14 Claims, No Drawings

METHOD FOR THE SELECTIVE PRODUCTION OF ACETIC ACID BY CATALYTIC OXIDATION OF ETHANE AND/OR ETHYLENE

This application is a 371 of PCT/EP01/04987 filed May 3, 2001.

The present invention relates to a process for the selective preparation of acetic acid by catalytic gas-phase oxidation of ethane and/or ethylene in the presence of a molybdenum- and palladium-containing catalyst.

The oxidative dehydrogenation of ethane to ethylene in the gas phase at temperatures >500° C. is disclosed, for example, in U.S. Pat. No. 4,250,346, U.S. Pat. No. 4,524,236 and U.S. Pat. No. 4,568,790.

Thus, U.S. Pat. No. 4,250,346 describes the use of a catalyst composition comprising the elements molybdenum, X and Y in the ratio a:b:c for conversion of ethane into ethylene, where X is Cr, Mn, Nb, Ta, Ti, V and/or W, and Y is Bi, Ce, Co, Cu, Fe, K, Mg, Ni, P, Pb, Sb, Si, Sn, Tl and/or U, and a is 1, b is from 0.05 to 1, and c is from 0 to 2. The total value of c for Co, Ni and/or Fe must be less than 0.5.

The reaction is preferably carried out in the presence of added water. The catalysts disclosed can likewise be used for the oxidation of ethane to acetic acid, the efficiency of the conversion to acetic acid being about 18%, with an ethane conversion of 7.5%.

The abovementioned specifications are principally concerned with the preparation of ethylene, less with the specific preparation of acetic acid.

By contrast, EP-B-0 294 845 describes a process for the selective preparation of acetic acid from ethane, ethylene or mixtures thereof with oxygen in the presence of a catalyst mixture which comprises at least A.) a calcined catalyst of the formula $Mo_xV_y$ or $Mo_xV_yZ_y$, in which Z can be one or more of the metals Li, Na, Be, Mg, Ca, Sr, Ba, Zn, Cd, Hg, Sc, Y, La, Ce, Al, Tl, Ti, Zr, Hf, Pb, Nb, Ta, As, Sb, Bi, Cr, W, U, Te, Fe, Co and Ni, and x is from 0.5 to 0.9, y is from 0.1 to 0.4, and z is from 0.001 to 1, and B.) an ethylene hydration catalyst and/or ethylene oxidation catalyst. The second catalyst component B is, in particular, a molecular sieve catalyst or a palladium-containing oxidation catalyst.

On use of the catalyst mixture described and feeding of a gas mixture consisting of ethane, oxygen, nitrogen and steam through the catalyst-containing reactor, the maximum selectivity is 27% with an ethane conversion of 7%. The high conversion rates of ethane are, according to EP 0 294 845, only achieved with the catalyst mixture described, but not in a single catalyst comprising components A and B.

A further process for the preparation of a product comprising ethylene and/or acetic acid is described in EP-B-0 407 091. In this process, ethane and/or ethylene and a gas containing molecular oxygen is brought into contact at elevated temperature with a catalyst composition comprising the elements A, X and Y. A here is $Mo_dRe_eW_f$, X is Cr, Mn, Nb, Ta, Ti, V and/or W, and Y is Bi, Ce, Co, Cu, Fe, K, Mg, Ni, P, Pb, Sb, Si, Sn, Tl and/or U. The maximum selectivities which were achieved on use of the catalyst described in the oxidation of ethane to acetic acid are 78%. Carbon dioxide, carbon monoxide and ethylene are formed as further by-products.

DE 19620542 describes a process for the selective preparation of acetic acid from a gaseous feed of ethane, ethylene or mixtures thereof and oxygen at elevated temperature, wherein the gaseous feed is combined with a catalyst which comprises the elements a:b:c:d:e in combination with oxygen: $Mo_aPd_bRe_cX_dY_e$, where the symbols X and Y are defined as follows: X=Cr, Mn, Nb, B, Ta, Ti, V and/or W; Y=Bi, Ce, Co, Cu, Te, Fe, Li, K, Na, Rb, Be, Mg, Ca, Sr, Ba, Ni, P, Pb, Sb, Si, Sn, Tl, and/or U; the indices a, b, c, d and e are the gram-atom ratios of the corresponding elements, where a=1, b>0, c>0, d=0.05 to 2, e=0 to 3. In the examples given, ethane conversions of up to 8% and acetic acid selectivities of up to 91% are achieved at 280° C. and 15 bar.

DE 19630832 describes a process for the selective preparation of acetic acid from a gaseous feed of ethane, ethylene or mixtures thereof and oxygen at elevated temperature. The feed is combined here with a catalyst which comprises the elements Mo, Pd, X and Y in combination with oxygen.

X here is one or more elements selected from the group consisting of Cr, Mn, Nb, Ta, Ti, V, Te and W, and Y is one or more elements selected from the group consisting of B, Al, Ga, In Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Tl and U. The gram-atom ratios for the corresponding elements are indicated here as follows: a (Mo)=1; b (Pd)>0; c (X)>0; and d (Y)=0–2.

The catalysts described in the abovementioned application exhibit a maximum space-time yield of 149 kg/(hm$^3$) with an acetic-acid selectivity of >60 mol %. Space-time yields characterize the amount of acetic acid produced per time and catalyst volume.

The invention WO 9847850 relates to a process for the selective preparation of acetic acid from a gaseous feed of ethane, ethylene or mixtures thereof and oxygen at elevated temperature on a catalyst which comprises the elements W, X, Y and Z in the gram-atom ratios a:b:c:d in combination with oxygen: $W_aX_bY_cZ_d$, in which X is one or more elements selected from the group consisting of Pd, Pt, Ag and/or Au, Y is one or more elements selected from the group consisting of V, Nb, Cr, Mn, Fe, Sn, Sb, Cu, Zn, U, Ni and/or Bi, Z is one or more elements selected from the group consisting of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and/or Te, a=1, b>0, c>0, d=0 to 2, and to the catalyst itself.

At 250° C., 15 bar and a residence time of 20 s, an acetic-acid selectivity of 80% was achieved with an ethane conversion of 10%.

WO 00/14047 relates to a process for the preparation of acetic acid in which ethane and/or ethylene is reacted with a gas containing molecular oxygen in a fluidized-bed reactor in the presence of a microspheroidally fluidized solid oxidation catalyst, where at least 90% of said catalyst particles are smaller than 300 μm. The catalyst described is a compound of the composition $Mo_aW_bAg_cIr_dXeY_f$, where X is Nb or V, Y is one of the elements from the group consisting of Cr, Mn, Ta, Ti, B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Tl, U, Re and Pd; a to f are the gram ratios of the elements, where 0<a≦1, 0≦b<1, and a+b=1, 0<(c+d)≦0.1, 0<e≦2, and 0≦f≦2. The examples given achieve a maximum space-time yield of acetic acid of 354.4 kg/(m$^3$h) for the oxidation of ethane to acetic acid and a space-time yield of acetic acid of 258.52 kg/(m$^3$h) for the oxidation of ethylene to acetic acid.

In DE 19745902, it has been found that it is possible to oxidize ethane and/or ethylene to acetic acid under relatively mild conditions, in a simple manner and with high selectivity and excellent space-time yields using a catalyst which comprises the elements molybdenum and palladium and one or more elements from the group consisting of chromium, manganese, niobium, tantalum, titanium, vanadium, tellurium and/or tungsten.

This invention DE 19745902 thus relates to a process for the selective preparation of acetic acid from a gaseous feed of ethane, ethylene or mixtures thereof and oxygen at elevated temperature, in which the gaseous feed is combined with a catalyst which comprises the elements Mo, Pd, X and Y in the gram-atom ratios a:b:c:d in combination with oxygen: $Mo_aPd_bX_cY_d$; and the symbols X and Y have the following meanings: X is one or more elements selected from the group consisting of Cr, Mn, Ta, Ti, V, Te and W, in particular V and W; Y is one or more elements selected from the group consisting of B, Al, Ga, In, Pt, Zn, Cd, Bi, Ce, Co, Cu, Rh, Ir, Au, Ag, Fe, Ru, Os, K, Rb, Cs, Mg, Ca, Sr, Ba, Nb, Zr, Hf, Ni, P, Pb, Sb, Si, Sn, Tl and U, in particular Nb, Ca, Sb and Li. The indices a, b, c and d are the gram-atom ratios of the corresponding elements, where a=1, b=0.0001 to 0.01, c=0.4 to 1, and d=0.005 to 1. If X and Y are a plurality of different elements, the indices c and d may likewise adopt a plurality of different values.

Said invention furthermore relates to a catalyst for the selective preparation of acetic acid, comprising the elements Mo, Pd, X and Y in the gram-atom ratios a:b:c:d in combination with oxygen. Gram-atom ratios a:b:c:d are preferably in the following ranges: a=1; b=0.0001 to 0.005; c=0.5 to 0.8, and d=0.01 to 0.3.

Palladium contents in the catalyst which are above the stated upper limit have an advantageous effect on the formation of carbon dioxide in the process described in DE 19745902. Furthermore, higher palladium contents are generally also avoided because they unnecessarily increase the cost of the catalyst. By contrast, a preferential action on the formation of ethylene is observed at palladium contents below the stated limit.

The catalyst used in DE 19745902 preferably comprises, besides the elements molybdenum and palladium, also vanadium, niobium, antimony and calcium in combination with oxygen. The gram-atom ratios $a:b:c^1:d^1:d^2:d^3$ for the elements Mo:Pd:V:Nb:Sb:Ca are preferably as follows: a (Mo) =1; b (Pd)=0.0001 to 0.005, in particular 0.0001 to 0.001; $c^1$ (V)=0.4 to 1.0; $d^1$ (Nb)=0.01 to 0.2; $d^2$ (Sb)=0.01 to 0.3; $d^3$ (Ca)=0.01 to 0.3.

The space-time yield achieved in DE 19745902 under Example 7 was 470 kg/(hm$^3$) at 310° C., 15 bar and a residence time of 7 s.

WO 00/00284 describes a catalyst system based on MoVNbPd, MoVLaPd or mixtures thereof for the preparation of acetic acid from ethylene. The examples indicated have a maximum space-time yield of 1291 kg/(m$^3$h) with an ethylene conversion of 63.43% and an acetic-acid selectivity of 78.03%.

The abovementioned patents make it clear that although space-time yields of acetic acid of up to 1291 kg/(m$^3$h) can be achieved in the oxidation of ethylene, the space-time yields of acetic acid in the oxidative reaction of ethane remain, however, significantly below this space-time yield which can be achieved for the oxidation of ethylene owing to the greater difficulty in activating ethane compared with ethylene. In DE-A-197 45 902, the greatest space-time yield of acetic acid achieved hitherto of 470 kg/(m$^3$h) is achieved for the oxidation of ethane. Higher space-time yields are desirable, since this would allow the size of the reactors and the amount of circulated gas to be reduced.

The object is therefore to provide a catalyst and a process which allow ethane and/or ethylene to be oxidized specifically to acetic acid in a simple manner and with high selectivity and space-time yield under the mildest possible reaction conditions.

The present invention describes a modified method for the preparation of catalysts described in DE-A-197 45 902 of similar composition which result in improved catalytic properties of the stated catalysts. One of the particular features of the present invention is that, using the catalyst described, besides the oxidation of ethylene also the considerably more difficult oxidation of ethane under optimized reaction conditions results in high ethane conversions, high acetic-acid selectivities and particularly in high acetic-acid space-time yields compared with said patents.

In DE-A-197 45 902, the catalysts were prepared by a conventional process starting from a slurry, in particular an aqueous solution comprising the individual starting components of the elements in accordance with their proportions. The starting materials for the individual components for the preparation of the catalyst according to the invention were, besides the oxides, preferably water-soluble substances, such as ammonium salts, nitrates, sulfates, halides, hydroxides and salts of organic acids which can be converted into the corresponding oxides by warming. For mixing of the components, aqueous solutions or suspensions of the metal salts were prepared and mixed. In the case of molybdenum, it was recommended, owing to the commercial availability, to employ the corresponding molybdates, such as, for example, ammonium molybdate, as starting compounds. The palladium compounds employed were, for example, palladium(II) chloride, palladium(II) sulfate, palladium(II) tetraamine nitrate, palladium(II) nitrate and palladium(II) acetylacetonate.

The present invention describes the preparation of the catalyst by a different method using different starting materials than those described in DE-A-197 45 902. Thus, instead of niobium oxalate, use is made of a niobium ammonium salt, preferably niobium ammonium oxalate having the composition $X_3NbO(C_2O_4)_3+X_2NbO(OH)(C_2O_4)_2$, where $X=H^+$ or $NH_4^+$ (manufacturer: H. C. Starck), which can have an Nb content of at least 19% by weight, ammonia contents of from 0 to 12% by weight and typical oxalate contents of from 50 to 65% by weight. Surprisingly, it has been found that the use of niobium ammonium salt, such as niobium ammonium oxalate, as niobium source results in better catalytic properties, which can be essentially attributed to a different Nb distribution in the catalyst compared with DE-A-197 45 902. In addition, the catalyst preparation method described in DE-A-197 45 902 is also modified in that palladium acetate is dissolved in an alcohol, in particular in ethanol, and not in acetone. This procedure also results in improved catalytic activities, which is essentially attributable to improved distribution of Pd in the mixture as a whole.

The present invention thus also relates to a niobium-containing catalyst of the abovementioned type which is obtainable by using a niobium ammonium salt, for example a niobium ammonium carboxylate, as niobium source.

The resultant reaction mixture is then stirred at from 50 to 100° C. for from 5 minutes to 5 hours. The water is subsequently removed, and the catalyst which remains is dried at a temperature of from 50 to 150° C., in particular from 80 to 120° C.

In the case where the resultant catalyst is subsequently subjected to a calcination process, it is advisable to calcine the dried and powdered catalyst at a temperature in the range from 100° C. to 800° C., in particular from 200 to 500° C., in the presence of nitrogen, oxygen or an oxygen-containing gas. The calcination can be carried out in a muffle furnace, but better in a rotary kiln, in which the corresponding gas flows continuously through the catalyst, which in turn results in improved homogeneity of the catalyst compared with the catalysts described in DE 19745902. The calcination duration is from 2 to 24 hours.

The catalyst can be employed without a corresponding support material or mixed with one or applied to one. Conventional support materials are suitable, such as, for example, porous silicon dioxide, ignited silicon dioxide, kieselguhr, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide, but also glass, carbon-fiber, metal-oxide or metal networks or corresponding monoliths.

Preferred support materials have a surface area of less than 100 m$^2$/g. Preferred support materials are silicon dioxide and aluminum oxide of low specific surface area. The catalyst can be employed after shaping as a regularly or irregularly shaped support element, but also in powder form as heterogeneous oxidation catalyst.

The reaction can be carried out in a fluidized bed or a fixed-bed reactor. For use in a fluidized bed, the catalyst is prepared by conventional processes, for example agglomeration, in such a way that a preferred particle size distribution in the range from 10 to 200 μm can be achieved.

The gaseous feed comprises ethane and/or ethylene, which are fed to the reactor as pure gases or in the form of a mixture with one or more other gases. Suitable as such additional or carrier gases are, for example, nitrogen, methane, carbon monoxide, carbon dioxide, air and/or steam. The gas containing molecular oxygen can be air or a gas which is richer or poorer in molecular oxygen than air, for example oxygen. The content of steam can be in the range from 0 to 50% by volume. Higher steam concentrations would unnecessarily increase the cost of work-up of the aqueous acetic acid formed for technical reasons. For this reason, the steam concentration in the feed has been reduced further in the examples of the present invention compared with the examples indicated in DE 19745902, which would result in a significant cost saving in the work-up of acetic acid. The ratio between ethane/ethylene and oxygen is advantageously in the range from 1:1 to 10:1, preferably from 2:1 to 8:1. Higher oxygen contents are preferred, since the achievable ethane conversion and thus the yield of acetic acid are higher. It is preferred to add oxygen or the gas containing molecular oxygen in a concentration range outside the explosion limits under reaction conditions, since this simplifies performance of the process. However, it is also possible to set the ethane/ethylene to oxygen ratio within the explosion limits.

The reaction is carried out at temperatures of from 200 to 500° C., preferably from 200 to 400° C. The pressure may be atmospheric or superatmospheric, for example in the range from 1 to 50 bar, preferably from 1 to 30 bar.

The reaction can be carried out in a fixed-bed or fluidized-bed reactor. In an advantageous procedure, ethane is firstly mixed with the inert gases, such as nitrogen or steam, before oxygen or the gas containing molecular oxygen is fed in. The mixed gases are preferably preheated to the reaction temperature in a preheating zone before the gas mixture is brought into contact with the catalyst. Acetic acid is separated off from the reactor offgas by condensation. The remaining gases are fed back to the reactor inlets, where oxygen or the gas containing molecular oxygen and ethane and/or ethylene is metered in.

In a comparison of the catalysts according to the invention with those known from the prior art, it is found that higher space-time yields and acetic-acid selectivities are achieved with the present catalysts under identical reaction conditions (reaction entry gas, pressure, temperature).

On use of the catalyst according to the invention, the selectivity in the oxidation of ethane and/or ethylene to acetic acid is ≧70 mol %, preferably ≧80 mol %, in particular ≧90 mol %, and the space-time yield is >470 kg/(hm$^3$), in particular >500 kg/(hm$^3$), preferably >550 kg/(hm$^3$), enabling an increase in the acetic-acid yields to be achieved in a simple manner with simultaneous reduction in the amount of undesired by-products formed by means of the process according to the invention compared with the prior art.

EXAMPLES

The catalyst composition shown in the example is given in relative atom ratios.

Catalyst Preparation:

Catalyst (I):

A catalyst of the following composition was prepared:
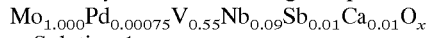
$Mo_{1.000}Pd_{0.00075}V_{0.55}Nb_{0.09}Sb_{0.01}Ca_{0.01}O_x$ Solution 1:

80 g of ammonium molybdate $(NH_4)_6Mo_7O_{24} \times 4H_2O$ (Riedel-de Haen) in 400 ml of water.

Solution 2:

29.4 g of ammonium metavanadate $NH_4VO_3$ (Riedel-de Haen) in 400 ml of water.

Solution 3:

19.01 g of niobium ammonium oxalate (H. C. Starck), 1.92 g of antimony oxalate $Sb_2(C_2O_4)_3$ (Pfaltz & Bauer), 1.34 g of calcium nitrate $Ca(NO_3)_2 \times 4H_2O$ (Riedel-de Haen) in 200 ml of water.

Solution 4:

0.078 g of palladium(II) acetate $(CH_3CO_2)_2Pd$ (Aldrich) in 200 ml of ethanol.

Aqueous solutions 1 to 3 are stirred separately at 70° C. for 15 minutes. The third solution is then added to the second. The combined mixtures are stirred at 70° C. for 15 minutes before these are added to the first mixture. Solution 4 is then added. The resultant mixture is stirred at 70° C. for 15 minutes and subsequently evaporated to a volume of 800 ml. The mixture is spray-dried and calcined in static air at 120° C. for 2 hours and at 300° C. for 5 hours. The catalyst is then ground slightly in a mortar and pressed to give tablets. These are crushed over a sieve in order to obtain a sieve fraction of from 0.35 to 0.7 mm.

Method for Catalyst Testing:

5 or 10 ml of the catalyst were loaded into a steel reactor with an internal diameter of 14 mm. The catalyst was heated to 250° C. under a stream of air. The pressure was subsequently adjusted by means of a prepressure regulator. The desired ethane:oxygen:nitrogen mixture was metered into an evaporator zone with water, where water was evaporated and mixed with the gases. The reaction temperature was measured in the catalyst bed using a thermocouple. The reaction gas was analyzed on-line by gas chromatography.

In the examples, the following terms are defined as:

$$\text{Ethane conversion } (\%) = ([CO]/2 + [CO_2]/2 + [C_2H_4] + [CH_3COOH])/([CO]/2 + [CO_2]/2 + [C_2H_4] + [C_2H_6] + [CH_3COOH]) * 100$$

Ethylene selectivity (%)=([C$_2$H$_4$])/([CO]/2+[CO$_2$]/2+ [C$_2$H$_4$]+[CH$_3$COOH])*100

Acetic-acid selectivity (%)=([CH$_3$COOH])/([CO]/2+ [CO$_2$]/2+[C$_2$H$_4$]+[CH$_3$COOH])*100 in which

[ ]=concentration in mol %, and

[C$_2$H$_6$]=concentration of the unreacted ethane.

The residence time is defined as:

θ (s)=bulk volume of the catalyst (ml)/volume flow rate of the gas through the reactor based on the reaction conditions (ml/s), STY denotes space-time yield in kg of acetic acid per hour and m$^3$ of catalyst.

Performance of the Reaction:

The ethane/oxygen/nitrogen ratio in the reaction gas was 5/1/4. The proportion of steam in the reaction mixture was set to values less than or equal to 20%. Since the space-time yield is dependent on the reaction pressure, all experimental examples were carried out at 15 bar for reasons of comparability. The reaction conditions and results are shown in Table 1.

TABLE 1

Results of catalytic studies of the oxidation of ethane to acetic acid on catalyst (I)

| | Reaction conditions | | | | | | Results | | | |
|---|---|---|---|---|---|---|---|---|---|---|
| | | | Reaction gas composition | | | | Conversion | Selectivity | | Space-time yield |
| Ex No. | T [°C.] | θ [s] | V(C$_2$H$_6$) [ml/s] | V(O$_2$) [ml/s] | V(N$_2$) [ml/s] | V(H$_2$O) [g/h] | X(C$_2$H$_6$) [%] | S(HOAc) [%] | S(C$_2$H$_4$) [%] | S(CO + CO$_2$) [%] | STY(HOAc) [kg/(hm$^3$)] |
| 1 | 280 | 14.8 | 1.0 | 0.2 | 0.8 | 1.4 | 13.3 | 91.5 | 0.7 | 7.8 | 235 |
| 2 | 280 | 7.4 | 2.0 | 0.4 | 1.6 | 2.9 | 10.5 | 90.4 | 3.5 | 6.0 | 362 |
| 3 | 300 | 7.1 | 2.0 | 0.4 | 1.6 | 2.9 | 13.2 | 89.0 | 2.0 | 9.0 | 447 |
| 4 | 300 | 4.8 | 3.0 | 0.6 | 2.4 | 4.3 | 11.3 | 87.2 | 5.5 | 7.3 | 564 |
| 5 | 300 | 4.1 | 3.5 | 0.7 | 2.8 | 5.0 | 10.2 | 86.2 | 7.4 | 6.4 | 584 |
| 6 | 300 | 3.7 | 4.0 | 0.8 | 3.2 | 5.0 | 9.9 | 84.1 | 9.2 | 6.6 | 630 |

Table 1 shows that the reduction in the residence time for the same reaction gas composition and at a reaction temperature of 280° C. results in a negligible decrease in conversion, constant acetic-acid selectivity, but a one-and-a-half-fold increased space-time yield (cf. experiments 1 and 2). A further reduction in the residence time at 300° C. (cf. experiments 3 and 4) with comparable conversions and selectivities results in a further increase in the space-time yield. Compared with experiment 4, the water content in the starting gas stream is also reduced in experiments 5 and 6 in addition to a further reduction in the residence time. For comparable conversions and acetic-acid selectivities, it was possible to further increase the space-time yield to 630 kg/(hm$^3$). It should also be particularly emphasized here that the marginal reduction in the acetic-acid selectivity compared with experiments 1 and 4 is not attributable to increased formation of total oxidation products, but instead ethylene is preferentially formed besides acetic acid owing to the low water content in the feed and can be circulated as valuable product and further oxidized to acetic acid.

The invention claimed is:

1. A continuous process for the selective preparation of acetic acid from a gaseous feed of ethane, ethylene or mixtures thereof and oxygen at elevated temperature, in which the gaseous feed is brought together with a catalyst comprising the elements Mo, Pd, X and Y in gram-atom ratios a:b:c:d in combination with oxygen $$Mo_a Pd_b X_c Y_d \qquad \text{I}$$

where the symbols X and Y are as defined below:

X is one or more elements selected from the group consisting of Cr, Mn, Ta, Ti, V, Te and W, Y is one or more elements selected from the group consisting of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Ti and U but shall be at least Nb;

the indices a, b, c and d are the gram-atom ratios of the corresponding elements, where a=1;

b=from 0.0001 to 0.01;

c=from 0.04 to 1; and d=from 0.005 to 1, and in which the residence times and the composition of the gaseous feed are selected in such a way that the space-time yield in the oxidation to acetic acid is >470 kg/(hm$^3$), with the proviso that the catalyst is obtained by the use of a niobium ammonium carboxylate as niobium source.

2. The process of claim 1, wherein niobium ammonium oxalate is used as niobium source.

3. The process of claim 1, wherein the temperature is in the range from 200 to 500° C.

4. The process of claim 1, wherein the pressure in the reactor is in the range from 1 to 50 bar.

5. The process of claim 1, wherein b is in the range from 0.0001 to 0.001.

6. The process of claim 1, wherein ethane mixed with at least one further gas is fed to the reactor.

7. The process as claimed in claim 6, wherein the further gas fed in is nitrogen, oxygen, methane, carbon monoxide, carbon dioxide, ethylene and/or steam.

8. The process of claim 1, wherein the catalyst is mixed with a support material or immobilized on a support material.

9. The process of claim 1, wherein the selectivity of the oxidation reaction of ethane and/or ethylene to acetic acid is >70 mol %.

10. The process of claim 1, wherein the catalyst comprises Pd introduced in the form of an alcoholic solution of palladium acetate.

11. A catalyst for the selective oxidation of ethane, ethylene or mixtures thereof and oxygen, comprising the elements Mo, Pd, X and Y in gram-atom ratios a:b:c:d in combination with oxygen $$Mo_a Pd_b X_c Y_d \qquad \text{I}$$

where the symbols X and Y are as defined below:
- X is one or more elements selected from the group consisting of Cr, Mn, Ta, Ti, V, Te and W,
- Y is one or more elements selected from the group consisting of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Ti and U but shall be at least Nb;
- the indices a, b, c and d are the gram-atom ratios of the corresponding elements, where
  a=1;
  b=from 0.0001 to 0.01;
  c=from 0.04 to 1; and
  d=from 0.005 to 1, the space-time yield in the oxidation reaction is >470 kg/(hm³), with the proviso that the catalyst is obtainable by the use of a niobium ammonium carboxylate as niobium source.

12. A catalyst as claimed in claim 11, where niobium oxalate is used as niobium source.

13. The catalyst as claimed in claim 11, where the Pd has been introduced in the form of an alcoholic solution of palladium acetate.

14. A continuous process for the selective preparation of acetic acid from a gaseous feed of ethane, ethylene or mixtures thereof and oxygen at elevated temperature, in which the gaseous feed is brought together with a catalyst comprising the elements Mo, Pd, X and Y in gram-atom ratios a:b:c:d in combination with oxygen $$Mo_a Pd_b X_c Y_d \qquad \text{I}$$

where the symbols X and Y are as defined below:
- X is one or more elements selected from the group consisting of Cr, Mn, Ta, Ti, V, Te and W,
- Y is one or more elements selected from the group consisting of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Ti and U but shall be at least Nb;
- the indices a, b, c and d are the gram-atom ratios of the corresponding elements, where
  a=1;
  b=from 0.0001 to 0.01;
  c=from 0.04 to 1; and
  d=from 0.005 to 1, and in which the residence times and the composition of the gaseous feed are selected in such a way that the space-time yield in the oxidation to acetic acid is >470 kg/(hm³), with the proviso that the catalyst is obtainable by the use of a niobium ammonium oxalate as niobium source and that Pd is introduced in the form of an alcoholic solution of palladium acetate.

* * * * *

UNITED STATES PATENT AND TRADEMARK OFFICE
CERTIFICATE OF CORRECTION

PATENT NO. : 7,015,355 B2 Page 1 of 1
APPLICATION NO. : 10/258758
DATED : March 21, 2006
INVENTOR(S) : Sabine Zeyss et al.

It is certified that error appears in the above-identified patent and that said Letters Patent is hereby corrected as shown below:

col. 8, line 18, change "0.04" to -- 0.4 --.

col. 9, line 19, change "0.04" to -- 0.4 --.

line 22, change "obtainable" to -- obtained --.

col. 10, line 20, change "0.04" to -- 0.4 --.

line 25, change "obtainable" to -- obtained--.

Signed and Sealed this

Fifth Day of September, 2006

JON W. DUDAS
*Director of the United States Patent and Trademark Office*